United States Patent [19]
Machhammer et al.

[11] Patent Number: 5,831,124
[45] Date of Patent: Nov. 3, 1998

[54] PURIFICATION OF ACRYLIC ACID AND METHACRYLIC ACID

[75] Inventors: Otto Machhammer, Mannheim; Albrecht Dams, Wachenheim; Bernd Eck, Viernheim; Theo Proll, Bad Dürkheim, all of Germany

[73] Assignee: BASF Aktiengesellschaft, Ludwigshafen, Germany

[21] Appl. No.: 798,138

[22] Filed: Feb. 12, 1997

[30] Foreign Application Priority Data

Feb. 23, 1996 [DE] Germany ............... 196 06 877.0

[51] Int. Cl.⁶ .................................................. C07C 51/42
[52] U.S. Cl. ................................................... 562/600
[58] Field of Search ............................................ 562/600

[56] References Cited

U.S. PATENT DOCUMENTS

| | | | |
|---|---|---|---|
| 3,603,103 | 9/1971 | Richmond et al. | 62/58 |
| 3,663,375 | 5/1972 | Witheford | 203/15 |
| 4,599,144 | 7/1986 | Baleiko et al. | 203/15 |
| 5,426,221 | 6/1995 | Willersinn | 562/600 |
| 5,504,247 | 4/1996 | Saxer et al. | 562/600 |
| 5,523,480 | 6/1996 | Bauer, Jr. et al. | 562/599 |

FOREIGN PATENT DOCUMENTS

| | | |
|---|---|---|
| 0 616 998 | 9/1994 | European Pat. Off. |
| 0 675 100 | 10/1995 | European Pat. Off. |
| 21 36 396 | 2/1973 | Germany |

*Primary Examiner*—Gary Geist
*Assistant Examiner*—Rosalynd Keys
*Attorney, Agent, or Firm*—Oblon, Spivak, McClelland, Maier & Neustadt, P.C.

[57] ABSTRACT

Acrylic acid or methacrylic acid is purified by
  (a) subjecting a mixture comprising the acrylic acid or methacrylic acid to a sharply defined separation process essentially in the absence of an organic solvent, with the composition of the phase in which the acrylic acid or methacrylic acid accumulates remaining essentially constant when the composition of the other phases participating in the mass transfer changes, then taking off this phase and
  (b) subjecting at least a part of the remaining phase from stage(a) to a less sharply defined separation process and
  (c) feeding one of the phases formed in stage (b) to the sharply defined separation process in stage (a).

In addition, the invention provides a process for preparing acrylic acid or methacrylic acid which includes the above-mentioned purification process.

12 Claims, 6 Drawing Sheets

PURIFICATION OF ACRYLIC ACID AND METHACRYLIC ACID

The present invention relates to a process for purifying acrylic acid and methacrylic acid. In addition, the invention relates to a process for preparing acrylic acid or methacrylic acid using the purification process.

It is known that material mixtures can be separated using processes in which phases are present or are formed. Examples which may be mentioned are extraction or absorption in which liquid/liquid or gas/liquid phases are present. Thus, DE-A-21 64 767 describes a process for purifying acrylic acid in which an aqueous acrylic acid solution is extracted with an extractant, the extractant is separated from the extract in a distillation zone and subsequently, in a rectification zone, a mixture of acrylic acid and acetic acid is distilled off from the remaining part of the extract. DE-C 34 29 391 discloses a process for preparing acrylic acid in which the gas obtained in the catalytic oxidation of propene and/or acrolein is condensed in an acrylic acid receiver and the substances not condensed are collected by absorption in water. The resulting aqueous solution of acrylic acid is then distilled in a distillation column in the presence of an azeotrope former, with the acrylic acid being obtained in the bottom product from the distillation. A similar process is also described in EP-A-0 551 111.

In the article "Separation of binary mixtures by combining rectification and fractionating crystallization" Russian Chemical Industry, Vol. 25, 1993, No. 2, pages 6–13, G. A. Nosov et al. describe the separation of mixtures by combined rectification and fractional crystallization, with the mixture to be separated being fed to a rectification stage and the vapor leaving the rectification column being fed to a crystallization stage. There, the vapor is cooled, forming a crystal phase and mother liquor. After separating the crystalline fraction from the mother liquor, the latter is returned to the rectification column. The company brochure "Fraktionierte Kristallisation" from SULZER CHEM TECH, 1991 likewise describes the combined use of rectification and crystallization with recirculation for separating isomer mixtures. In the article "The attractions of melt static crystallization", Chemical Engineering, September 1995, pages 108–110, M. Hassene and G. Drouglazet describe static melt crystallization as a purification process which can be combined with distillation. In processes for preparing naphthalene, toluene derivatives or nitrobenzene, this combined process is used for final purification. The further article "Acrylic acid and acrylates", 91–2, February 1993, CHEM SYSTEMS, pages 22–26, describes how crude acrylic acid prepared by two-stage oxidation is separated off by solvent extraction after cooling and absorption in water. The further purified crude acrylic acid obtained is subsequently subjected to a purification process which can be a crystallization. This article gives no further details on this subject.

Japanese Patent 45-32417 discloses a process in which an aqueous acrylic acid solution or methacrylic acid solution which additionally contains acetic acid and propionic acid is extracted with heptane or toluene and water is subsequently removed from the extract by distillation. In the next stage, the remaining extract is cooled to from −20° to −80° C. to induce crystallization of acrylic acid or methacrylic acid. The crystals are separated off and the mother liquor is returned to the extraction process. According to this patent, the addition of an organic solvent or extractant is necessary since otherwise the solution solidifies on cooling without crystals being precipitated. JA-7032417 describes the purification of methacrylic acid by extracting the latter with butadiene, heptene or toluene, dehydrating the extract by distillation and subsequently crystallizing out the methacrylic acid by cooling to from −20° to −80° C. The crystals are separated off by filtration and the filtrate is recirculated. JA-7110535 describes a similar purification process for acrylic acid. In all the processes described in the three last-named documents, the crystallization is carried out in the presence of an organic solvent.

It is an object of the present invention to provide a process for purifying acrylic acid and methacrylic acid in which a higher yield can be achieved together with high purity of the acids.

We have found that this object is achieved by combined use of a sharply defined and a less sharply defined separation process, where the phase remaining from the sharply defined separation process, which is not enriched with acid, is at least partially recirculated to the less sharply defined separation process.

The present invention accordingly provides a process for purifying acrylic acid or methacrylic acid by means of separation processes in which phases are formed, which comprises (a) subjecting a mixture comprising the acrylic acid or methacrylic acid to a sharply defined separation process essentially in the absence of an organic solvent, with the composition of the phase in which the acrylic acid or methacrylic acid accumulates remaining essentially constant when the composition of the other phases participating in the mass transfer changes, then taking off this phase and (b) subjecting at least a part of the remaining phase from stage (a) to a less sharply defined separation process and (c) feeding one of the phases formed in stage (b) to the sharply defined separation process in stage (a).

In one embodiment, the present invention provides a process for preparing acrylic acid or methacrylic acid which comprises the following stages:

(I) catalytic gas-phase oxidation of propene or isobutene and/or acrolein or methacrolein to acrylic acid or methacrylic acid, with formation of a gaseous reaction product containing the acid, (II) absorption of the reaction product using a high-boiling solvent, (III) separation of the loaded solvent from stage (II) into the solvent and a crude acid by means of distillation, (IV) purification of the acrylic acid or methacrylic acid from the crude acid from stage (III) according to the purification process of the present invention, with the less sharply defined separation process being the absorption of stage (II) and/or the distillation of stage (III) and the sharply defined separation process being a crystallization.

Preferred embodiments of the invention are defined in the subclaims. Further and preferred features are indicated in FIGS. 1 to 6 and the description.

The separation processes used according to the present invention are separation processes in which phases are formed. According to the present invention, the sharply defined separation process is a process in which the phase in which the acrylic acid or methacrylic acid accumulates and/or in which these materials are predominantly present has a composition which remains essentially constant when the composition of the remaining phases participating in the mass transfer and/or coexisting phases changes. In particular, this is a separation process in which the composition of one of the phases formed is essentially independent of the composition of the material fed in. The sharply defined separation process is carried out essentially in the absence of an organic solvent, preferably in the complete absence of an organic solvent. The mixture to be purified in stage (a) preferably contains not more than 1% by weight, in particular not more than 0.1% by weight, of organic solvent, in each case based on 100% by weight of mixture to be purified. The sharply defined separation process selected is here subject to no restriction. Advantageously, it is a crystallization, a freezing out, an evaporation, a sublimation or a combination of these processes including the multiple use of these processes. Most preferred is crystallization, with this being carried out dynamically and/or statically.

Particularly preferred is dynamic crystallization or a combination of dynamic and static crystallization. In the latter embodiment, as described in EP-A-0 616 998, the residue of the dynamic crystallization is preferably fed to the static crystallization and the crystallized material from the static crystallization is fed to the dynamic crystallization. The way in which the dynamic and/or static crystallization is carried out is not critical here. In the static crystallization (e.g. U.S. Pat. No. 3,597,164 and FR 2 668 946), the liquid phase is moved only by free convection, while in the dynamic crystallization the liquid phase is moved by forced convection. The latter can be achieved by forced flow in apparatuses which are completely filled by the material flowing through them (cf. DE-A-2 606 364) or by feeding a trickling or falling film onto a cooled wall (DE 1 769 123 and EP-A-0 218 545). The dynamic and static crystallizations can each be carried out in one or more stages. Multistage processes are here advantageously carried out according to the countercurrent principle, in which, in each stage, the crystallized material is separated from the residue after crystallization and this crystallized material is fed to the respective stage having the next higher degree of purity, while the crystallization residue is fed to the respective stage having the next lower degree of purity. Usually, all stages which produce a crystallized material which is purer than the crude acid solution fed in are referred to as purification stages and all other stages are known as stripping stages. Static crystallization is advantageously used in the stripping stages when the yield of the acid is to be increased further.

According to the present invention, the less sharply defined separation process is a separation process which does not come under the above definition of the sharply defined separation process. In particular, it is a separation process in which the composition of the phases formed is dependent on the composition of the material fed in. The less sharply defined separation processes which come into question here are subject to no particular restriction. Advantageously, this process is a distillation, rectification, absorption, adsorption, extraction, supercritical extraction, a membrane separation process such as a pervaporation/vapor permeation, or a combination of these processes. Use is advantageously made of a distillation, rectification, absorption or extraction or a combination of these processes, including the multiple use of these processes. If a sharply defined and a less sharply defined separation process are viewed in terms of the work of separation and one separation stage, then for a constant work of separation a sharply defined separation process achieves a higher purity, while a less sharply defined separation process achieves a higher yield.

A particularly advantageous combination of sharply defined and less sharply defined separation processes is the combination of absorption, extraction and/or distillation with crystallization.

According to the present invention, the mixture to be purified or the starting material can be any material mixture containing acrylic acid or methacrylic acid. Particularly well suited is a mixture as obtained in the preparation of acrylic acid or methacrylic acid by oxidation of propene or isobutene, subsequent absorption with a high-boiling solvent and distillation or, after the oxidation, subsequent condensation or absorption with water and extraction. Such mixtures comprise the acid plus, as impurities, essentially at least one of the compounds selected from the group consisting of aldehydes, propionic acid and acetic acid. Such a mixture preferably contains acrylic acid or methacrylic acid in an amount of 90–99% by weight and impurities preferably in the following amounts, where all amounts are based on 100% by weight of the mixture: aldehydes from 0.05 to 2% by weight, propionic acid from 0.01 to 2% by weight and acetic acid from 0.05 to 2% by weight. Mixtures which are subjected to the sharply defined separation process in stage (a) contain essentially no organic solvent, preferably less than 1% by weight, in particular less than 0.1% by weight, particularly preferably less than 0.01% by weight, of organic solvent, in each case based on 100% by weight of mixture.

According to the process of the present invention, at least part of the phase depleted in acrylic acid or methacrylic acid remaining in stage (a) is fed to the less sharply defined separation process in stage (b). The most suitable feed ratio for the respective application can easily be determined by a person skilled in the art by means of customary experiments. Preference is given to feeding in from 1 to 100% by weight, in particular from 5 to 50% by weight, most preferably from 10 to 20% by weight, of the remaining phase.

In an advantageous embodiment of the invention, the phase enriched in acrylic acid or methacrylic acid is separated off in stage (c) and subjected to the sharply defined separation process in stage (a). It is possible for a starting material to be purified, which comprises acrylic acid or methacrylic acid, to be fed as a mixture to stage (a) and/or stage (b).

The present invention makes it possible, by appropriate selection of the amounts of the phase fed from stage (a) to stage (b), to correspondingly increase the yield of the acid while the purity of this material remains essentially constant.

Figure 1:
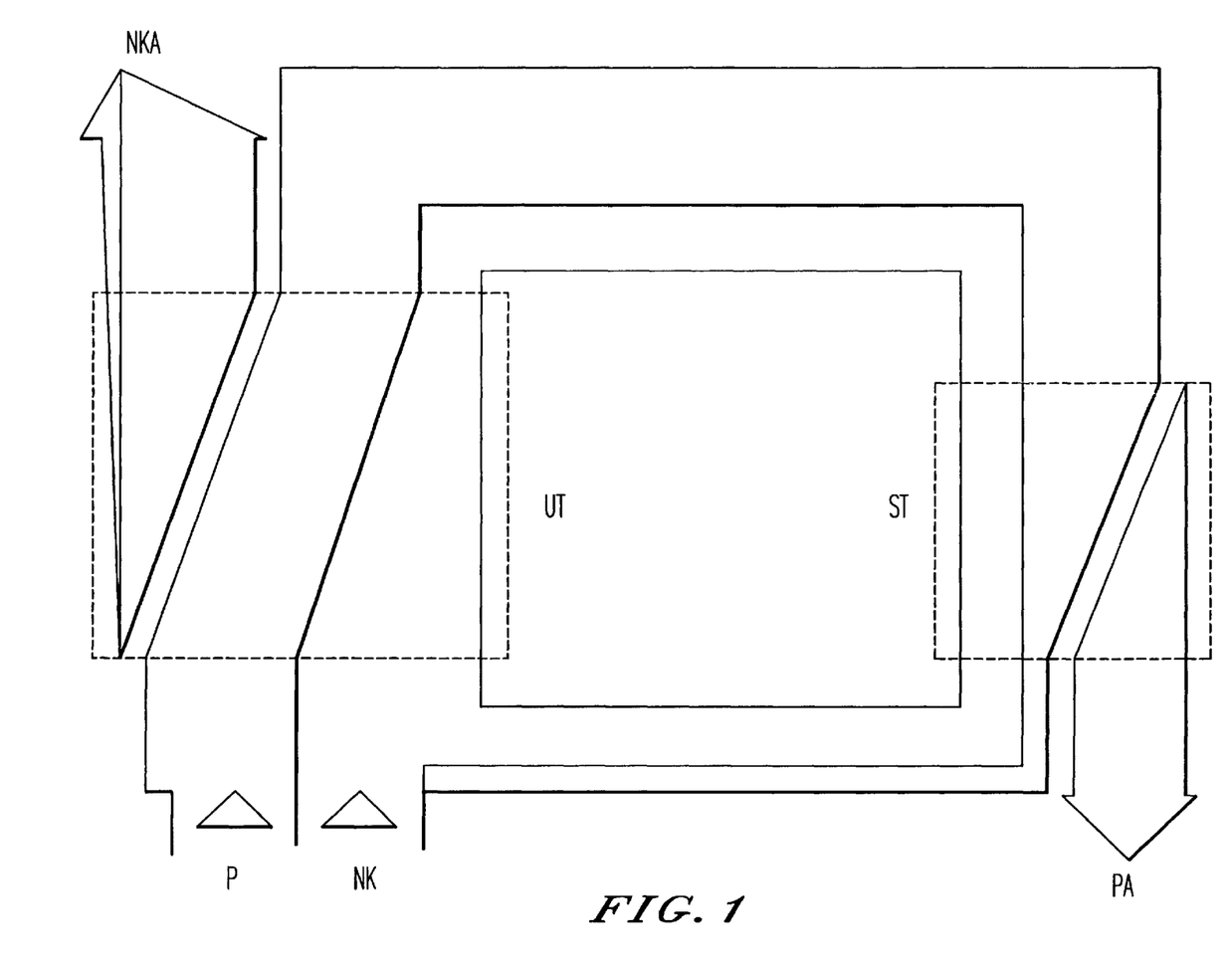
FIG. 1 shows an example of a preferred embodiment of the process of the present invention for purifying acrylic acid or methacrylic acid.

FIG. 1 shows an example of a preferred embodiment of the process of the present invention, in which starting material to be purified is fed in upstream of the less sharply defined separation process. The thickness of the arrows indicates the amounts of desired product (acrylic acid or methacrylic acid) and the undesired cocomponents (NK). The other references are: less sharply defined separation (UT), sharply defined separation (ST), product (P), product discharge (PA), cocomponent discharge (NKA).

In a preferred embodiment, the invention provides a process for preparing acrylic acid or methacrylic acid which comprises the stages (I) to (IV) as defined above. The individual stages are described below for acrylic acid. They apply in a similar manner to methacrylic acid, unless otherwise indicated.

Stage (I):

Stage (I) comprises the catalytic gas-phase reaction of propene and/or acrolein with molecular oxygen to give acrylic acid. In the case of methacrylic acid, a gas-phase reaction of isobutene and/or methacrolein with molecular oxygen occurs in a similar way. The gas-phase reaction can be carried out by known methods, in particular as described in the abovementioned documents. The reaction is advantageously carried out at from 200° to 400° C. As heterogeneous catalysts, preference is given to using oxidic multicomponent catalysts based on the oxides of molybdenum, chromium, vanadium and/or tellurium.

The reaction of propene to give acrylic acid is strongly exothermic. The reaction gas, which advantageously contains a diluent gas, eg. circulation gas (see below), atmospheric nitrogen and/or water vapor in addition to the starting materials and products, can therefore take up only a small part of the heat of reaction. Therefore, the reactors used are usually shell-and-tube heat exchangers which are charged with the oxidation catalyst and remove the major part of the heat liberated during the reaction by convection and radiation to the cooled tube walls.

However, stage (I) does not give pure acrylic acid, but a gaseous mixture which can comprise acrylic acid and, as cocomponents, essentially unreacted acrolein and/or propene, water vapor, carbon monoxide, carbon dioxide, nitrogen, oxygen, acetic acid, propionic acid, formaldehyde, further aldehydes and maleic anhydride. In particular, the reaction product mixture typically comprises, in each case given in % by weight based on the total reaction mixture, from 0.05 to 1% of propene and from 0.05 to 1% of acrolein, from 0.01 to 2% of propane, from 1 to 20% of water vapor, from 0.05 to 15% of carbon oxides, from 10 to 90% of nitrogen, from 0.05 to 5% of oxygen, from 0.05 to 2% of acetic acid, from 0.01 to 2% of propionic acid, from 0.05 to 1% of formaldehyde, from 0.05 to 2% of aldehydes and from 0.01 to 0.5% of maleic anhydride.

Stage (II):

In stage (II), the acrylic acid and part of the cocomponents are separated from the reaction gas by absorption with a high-boiling solvent. Suitable solvents for this purpose are all high-boiling solvents, in particular solvents having a boiling point above 160° C. Particularly suitable is a mixture of diphenyl ether and biphenyl, for example the commercially available mixture of 75% by weight of diphenyl ether and 25% by weight of biphenyl.

For the purposes of the present invention, the terms high boiler, intermediate boiler and low boiler and the corresponding adjectival terms designate compounds which have a boiling point higher than that of acrylic acid (high boilers) or compounds which have about the same boiling point as acrylic acid (intermediate boilers) or compounds which have a boiling point lower than that of acrylic acid (low boilers).

Advantageously, the hot reaction gas obtained from stage (I) is cooled by partial evaporation of the solvent in a suitable apparatus, eg. a direct condenser or quenching apparatus, prior to absorption. Suitable apparatuses for this purpose are, in particular, venturi scrubbers, bubble columns or spray condensers. In this cooling step, the high-boiling cocomponents of the reaction gas from stage (I) condense into the unvaporized solvent. In addition, the partial evaporation of the solvent is a purification step for the solvent. In a preferred embodiment of the invention, a substream of the unvaporized solvent, preferably from 1 to 10% of the mass flow fed to the absorption column, is taken off and subjected to solvent purification. In this solvent purification, the solvent is distilled over and the high-boiling cocomponents remain as a residue and can, if necessary after further concentration, be disposed of, eg. incinerated. This solvent distillation serves to avoid too high a concentration of high boilers in the solvent stream.

Absorption is carried out in a countercurrent absorption column which is preferably equipped with valve or dual-flow trays and has (unvaporized) solvent introduced at the top. The gaseous reaction product and any vaporized solvent are introduced into the column from below and are subsequently cooled to absorption temperature. Cooling is advantageously carried out by means of cooling circuits, ie. heated solvent is taken from the column, cooled in heat exchangers and fed to the column again at a point above the offtake point. In these solvent cooling circuits, not only the acrylic acid but also high- and intermediate-boiling cocomponents and vaporized solvent condense. As soon as the reaction gas stream has been cooled to the absorption temperature, the actual absorption takes place. Here, the residual acrylic acid remaining in the reaction gas is absorbed together with part of the low-boiling cocomponents.

The remaining reaction gas from stage (I) which is not absorbed is cooled further in order to separate off the condensable part of the low-boiling cocomponents, in particular water, formaldehyde and acetic acid, by condensation. This condensate is hereinafter referred to as acid water. The remaining gas stream, hereinafter referred to as circulation gas, consists predominantly of nitrogen, carbon oxides and unreacted starting materials. Part of this is preferably recirculated to the reaction stages as diluent gas.

A solvent stream loaded with acrylic acid, high- and intermediate-boiling cocomponents as well as a small amount of low-boiling cocomponents is taken from the bottom of the column used in stage (II) and, in a preferred embodiment of the invention, subjected to desorption. This is advantageously carried out in a column, which can preferably be fitted with valve or dual-flow trays or else with loose packing or arranged packing elements, in the presence of a stripping gas. The stripping gas used can be any inert gas or gas mixture, preferably a gas mixture of air and nitrogen since this is obtained in stage (I) when evaporating part of the solvent. In the desorption, the major part of the low boilers is stripped from the loaded solvent using part of the circulation gas which is taken off before stage (I). Since relatively large amounts of acrylic acid are also stripped out, this stream, hereinafter referred to as circulated stripping gas, is, for economic reasons, not discarded but advantageously recirculated, eg. to the stage in which the partial evaporation of the solvent is carried out or to the absorption column. Since the stripping gas is part of the circulation gas, it itself still contains appreciable amounts of low boilers. The performance of the column used for desorption can be improved if the low boilers are removed from the stripping gas prior to introduction into the column. Advantageously, this is carried out by purifying the stripping gas in a countercurrent scrubbing column using solvent worked up in the stage (III) described below.

A solvent stream loaded with acrylic acid and almost free of low boilers can then be taken from the bottom of the column used for desorption.

Stage (III):

In process stage (III), the acrylic acid together with the intermediate-boiling components and the remaining residue of low-boiling cocomponents is separated from the solvent.

This separation is carried out by means of distillation, with any distillation column being able to be used in principle. Advantageously, a column fitted with sieve trays, eg. dual-flow trays or crossbow sieve trays of metal, is used for this purpose. In the enrichment section of the column, the acrylic acid is distilled free of the solvent and the intermediate-boiling cocomponents such as maleic anhydride. To reduce the proportion of low boilers in the acrylic acid, the enrichment section of the column is advantageously lengthened and the acrylic acid is taken off from the column as a side stream. This acrylic acid is referred to as crude acrylic acid.

At the top of the column, after a partial condensation, a stream rich in low boilers is taken off. However, since this stream still contains acrylic acid, it is advantageously not discarded but returned to the absorption stage (II).

At the bottom of the column, the solvent which is free of low boilers and virtually free of acrylic acid is taken off and preferably mostly fed to the countercurrent scrubbing column in which the stripping gas from stage (II) is purified, in order to scrub the low boilers from the stripping gas. Subsequently, the virtually acrylic acid-free solvent is fed to the absorption column.

In a preferred embodiment of the invention, the acid water, which can still contain dissolved acrylic acid, is extracted with a small substream of the virtually acrylic acid-free solvent. In this acid water extraction, part of the acrylic acid is extracted into the solvent and thus recovered from the acid water. In the other direction, the acid water extracts the polar intermediate-boiling components from the solvent stream and thus avoids an accumulation of these components in the solvent circuit. The resulting stream comprising low and intermediate boilers can be further concentrated, which can be necessary, in particular, if environment protection regulations apply.

The crude acrylic acid obtained in stage (III) comprises, in each case based on the crude acrylic acid, preferably from 98 to 99.8% by weight, in particular from 98.5 to 99.5% by weight, of acrylic acid and from 0.2 to 2% by weight, in particular from 0.5 to 1.5% by weight, of impurities such as acetic acid, aldehydes and maleic anhydride. This acrylic acid may, if the purity requirements are not very high, be used for esterification.

Stage (IV):

The acrylic acid is separated from the crude acrylic acid obtained from stage (III) by means of dynamic crystallization or a combination of dynamic and static crystallization, with the resulting mother liquor (residue phase) not being discarded but being recirculated at least partially to the absorption stage (II) or distillation stage (III). Most preferred is recirculation to the absorption, since this makes possible a better separation of the cocomponents by low boiler scrubbing and low boiler stripping.

In stage (IV), the crude acrylic acid to be purified is introduced in liquid form into the crystallization apparatus and subsequently a solid phase which has a different composition from the liquid phase introduced is frozen out on the cooled surfaces. After a certain proportion of the acrylic acid fed in has been frozen out (advantageously 50–80%, in particular 60–70%), the remaining liquid residue phase is separated off. This is advantageously carried out by simply allowing the residue phase to flow away or pumping it away. The crystallization step can also be followed by further purification steps such as washing of the crystal layer (cf. DE 3 708 709) or sweating, ie. partial melting of contaminated crystal regions. The crystallization step is advantageously followed by a sweating step if the overall purifying action of a stage is to be improved.

If desired, the pure acrylic acid obtained in stage (IV) can be esterified by known methods.

Figure 2:
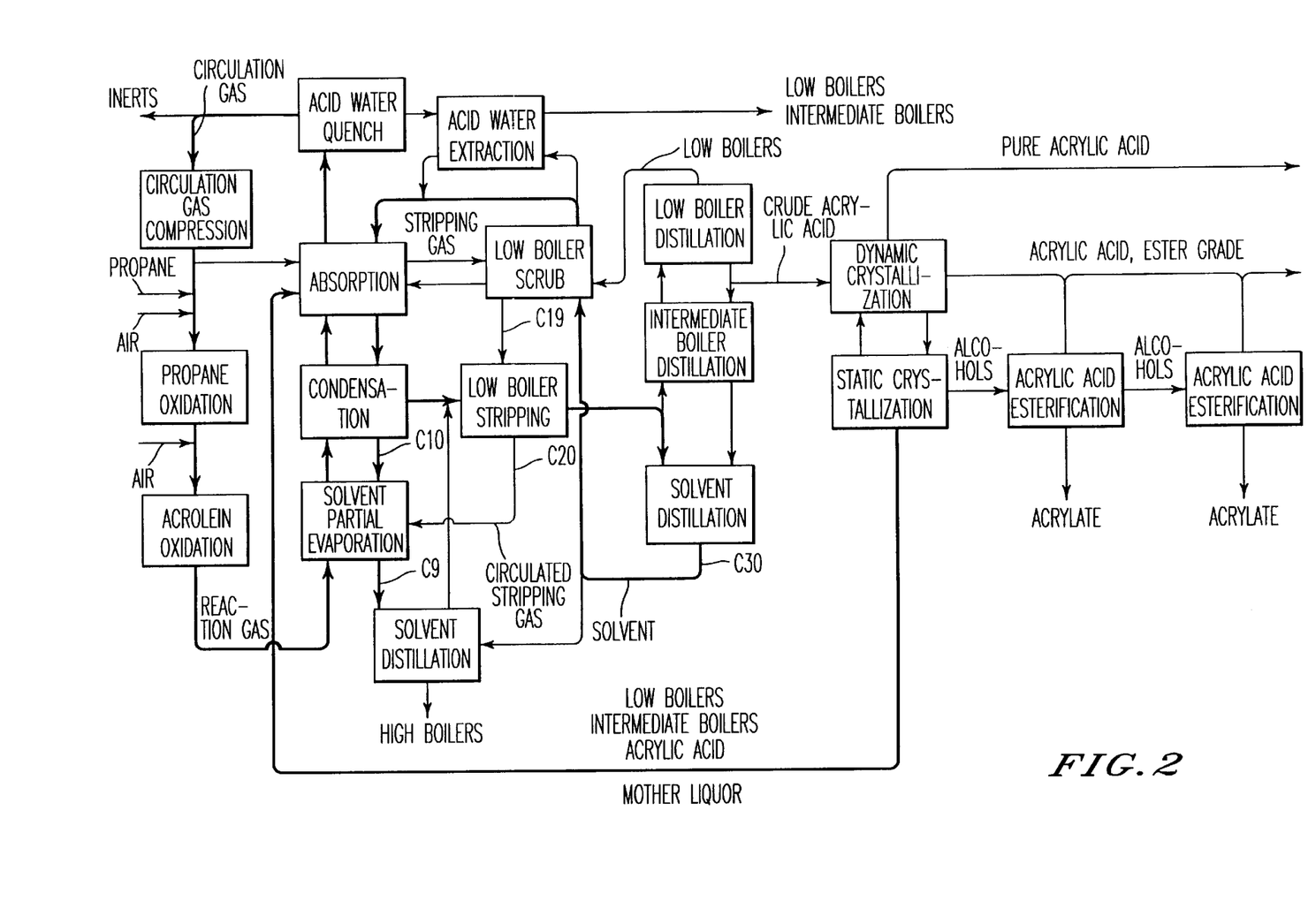
FIG. 2 shows a process flow diagram for preparing acrylic acid using a static and a dynamic crystallization.
Figure 3:
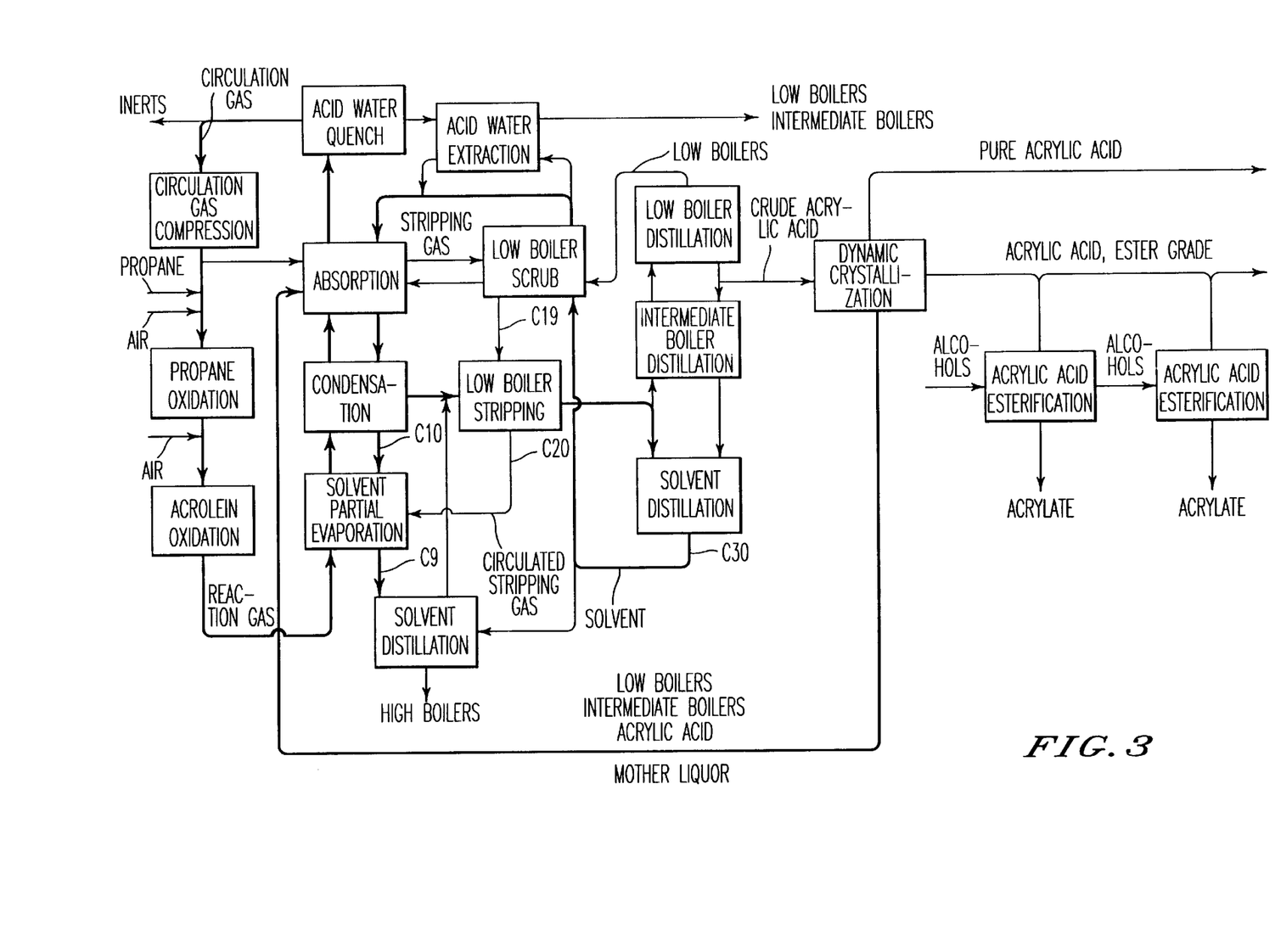
FIG. 3 shows a process flow diagram for preparing acrylic acid using a dynamic crystallization.

FIGS. 2 and 3 show a process flow diagram for preparing acrylic acid.

According to FIG. 2, the circulation gas which consists essentially of nitrogen, carbon oxides and unreacted starting materials is compressed and then fed together with propene and air to a reactor in which the heterogeneously catalyzed oxidation of propene to acrolein takes place. The resulting intermediate reaction gas is admixed with further air in order to carry out the heterogeneously catalyzed oxidation of acrolein in the second reactor.

The resulting hot, gaseous reaction product which contains acrylic acid is cooled by partial evaporation of the solvent in a direct condenser C9 prior to absorption. In this condenser, the high-boiling cocomponents of the reaction product condense into the unvaporized solvent. A substream from the direct condenser C9 is subjected to solvent distillation, with the solvent being distilled over and the high-boiling cocomponents being left behind. The latter can be further concentrated and disposed of, eg. incinerated.

The column C10, which is preferably a packed column, has (unvaporized) solvent introduced from above while the vaporized solvent and the gaseous reaction product are introduced into the column C10 from below and are subsequently cooled to the absorption temperature. Cooling is carried out by means of cooling circuits (not shown). In these cooling circuits, the vaporized solvent, the acrylic acid as well as all high- and intermediate-boiling cocomponents condense. After the entire reaction gas stream has been cooled to the absorption temperature, the actual absorption takes place. Here, the residual acrylic acid remaining in the reaction gas as well as part of the low-boiling cocomponents are absorbed. Subsequently, the remaining unabsorbed reaction gas is cooled further in order to separate the condensable part of the low-boiling cocomponents from the gas stream, shown in FIG. 1 as acid water quench. This condensate is referred to as acid water. Part of the remaining gas stream, the circulation gas, can then be recirculated as diluent gas to the reaction stages, as shown in FIG. 1.

At the bottom of the column C10, the solvent loaded with acrylic acid and cocomponents is taken off and fed to the desorption column C20. In the latter, the major part of the low boilers are stripped from the loaded solvent by means of part of the circulation gas which is taken from before the oxidation stages. Since this also strips out relatively large amounts of acrylic acid, this stream is, for example, recirculated to the direct condenser C9.

To improve the desorption performance of the column C20, the low boilers present in the stripping gas are removed prior to its introduction into the column C20. This is advantageously carried out by purifying the stripping gas in a countercurrent scrubbing column C19 using worked-up solvent from the column C30 described in more detail below.

In the next process step, a solvent stream which is loaded with acrylic acid and is almost free of low boilers is taken off from the bottom of the desorption column C20 and fed to the distillation column C30, which is preferably a sieve tray column. The high-boiling solvent and the intermediate-boiling cocomponents, eg. maleic anhydride, condense into the bottom of the column C30. Since the acrylic acid taken off at the top of the column C30 still contains appreciable amounts of low-boiling cocomponents, this proportion of low boilers is advantageously reduced by further lengthening the enrichment section of the column C30 and taking the acrylic acid from the column as a side stream. This acrylic acid is referred to as crude acrylic acid.

The stream rich in low boilers taken off at the top of the distillation column C30 is, since it still contains acrylic acid, advantageously recirculated to the absorption column C10.

The major part of the low boiler-free and virtually acrylic acid-free solvent taken off from the bottom of the distillation column C30 is fed to the countercurrent scrubbing column C19 in order to, as already mentioned above, scrub the low boilers from the stripping gas stream which goes to the desorption column C20. Subsequently, the virtually acrylic acid-free solvent is fed to the absorption column C10. A small substream of the virtually acrylic acid-free solvent from the bottom of the distillation column C30 is used to extract the acid water which still contains dissolved acrylic acid. In this acid water extraction, part of the acrylic acid is recovered from the acid water, while in the other direction the acid water extracts all polar components from the solvent substream. The acid water formed here can be pre-evaporated and subsequently incinerated.

The crude acrylic acid obtained from the side offtake of the distillation column C30 is subsequently subjected to a dynamic and static crystallization.

All of the mother liquor from the static crystallization is then returned to the absorption stage.

If desired, the pure acrylic acid obtained is then esterified with alcohols to give the desired acrylates.

FIG. 3 differs from FIG. 2 in that only a dynamic crystallization is provided in place of the dynamic and static crystallizations.

The process of the present invention thus offers the advantage that the total yield of the desired material and thus the total economics of the process is increased by recirculation. Furthermore, it offers the possibility of improving the economics even further by omitting a static crystallization.

The invention is illustrated by the following examples which represent preferred embodiments of the invention.

Figure 4:
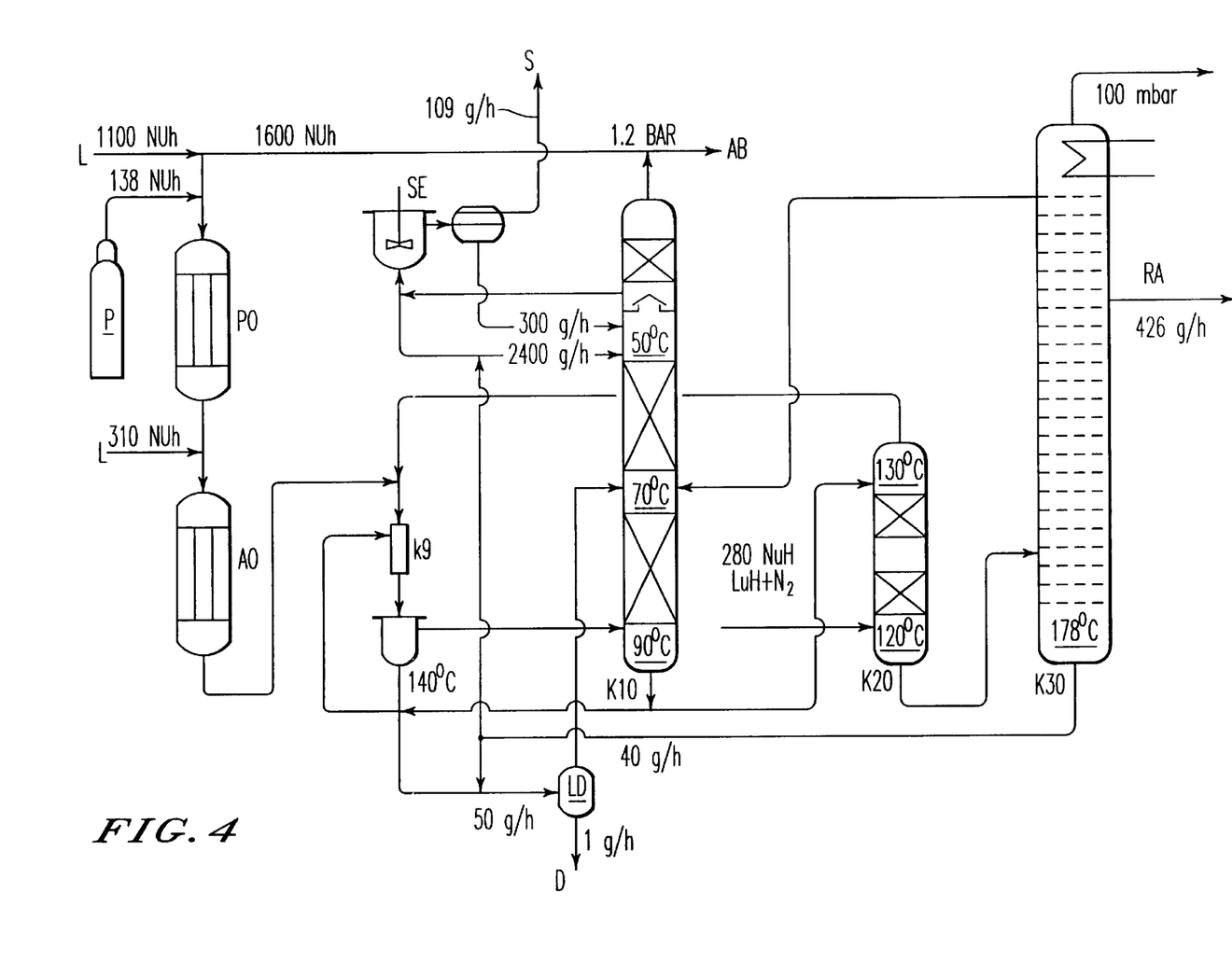
FIG. 4 shows an experimental arrangement for preparing crude acrylic acid.

In a miniplant, 426 g/h of crude acrylic acid (RA) were produced. The way in which the equipment items were connected, the amounts required and the operating parameters used are shown in FIG. 4. This figure shows the same columns and equipment items as in FIGS. 2 and 3, with the same numbers being used for corresponding items (additional: solvent distillation: LD; distillation residue: D; acid water: S; acid water extraction: SE; waste gas: AB). The oxidation of propene (P) with air (L) via acrolein (A) was carried out in two reaction tubes connected in series and having a diameter of 26 mm and a catalyst bed length of 2.5 m. The first tube (propene oxidation: PO) was charged with a coated catalyst as described in EP 575 897 and the second reaction tube (acrolein oxidation: AO) contained a coated catalyst as described in EP 609 750. The columns C10, C20 and C30 were mirrored and thermostated laboratory columns having a diameter of 50 mm. The direct condenser C9 was a venturi scrubber. The columns C10 and C20 were packed with 5 mm metal helices. The distillation column C30 was provided with sieve trays (dual-flow trays) made of metal. The holes in the sieve trays were configured such that effervescent layers could be formed.

DYNAMIC CRYSTALLIZATION

The dynamic crystallization was carried out in a crystallizer as is described in DE-A-26 06 364 (BASF), with the tube used being completely filled by the material flowing through it. The data for the crystallizer were as follows:

two passes with one tube (internal diameter 26 mm) per pass tube length 5 m variable speed centrifugal pump as primary circuit pump primary-side volume of unit about 11 l degree of freezing out about 45% (degree of freezing out=mass of crystallized material/mass of raw melt)

4 stage containers each having a volume of 100 l temperature control of the unit by means of a refrigeration unit and 4 bar steam via heat exchangers.

The unit was controlled by means of a process control system, with the program sequence for one stage being as follows:

1. filling of the primary circuit
2. emptying of the primary circuit and freezing-on of a nucleating layer
3. increase of temperature to about 2° C. below the melting point
4. filling of the primary circuit for crystallization
5. crystallization (temperature program)
6. pumping out of residual melt after completion of the crystallization
7. increasing the temperature to melt the crystal layer
8. pumping out molten crystallized material
9. commencement of a new stage.

The temperatures, pressures and volume flows are dependent on the respective stage being carried out.

STATIC LAYER CRYSTALLIZATION

The unit used for this purpose comprised a tube crystallizer of glass having an internal diameter of 80 mm and a length of 1 m. The temperature of the crystallizer was controlled via a glass jacket. The fill volume of the crystallizer was from 2.0 to 5.0 l (variable). The unit was heated/cooled via a thermostat, with the temperature being controlled by means of a programmed controller. The degree of freezing out (after sweating) was about 50%. The program sequence for a stage was as follows:

1. filling of the crystallizer
2. adjusting the temperature of the apparatus with contents (to about 1K above the melting point)
3. crystallization (temperature program)
4. draining the residual melt after completion of crystallization
5. sweating (temperature program)
6. melting of crystallized material
7. commencement of a new stage The temperatures are dependent on the respective stage being carried out.

The numerical values given in Examples 1 to 3 were obtained from the actual measurement results from a plurality of experiments.

EXAMPLE 1 (COMPARISON)

Figure 5:
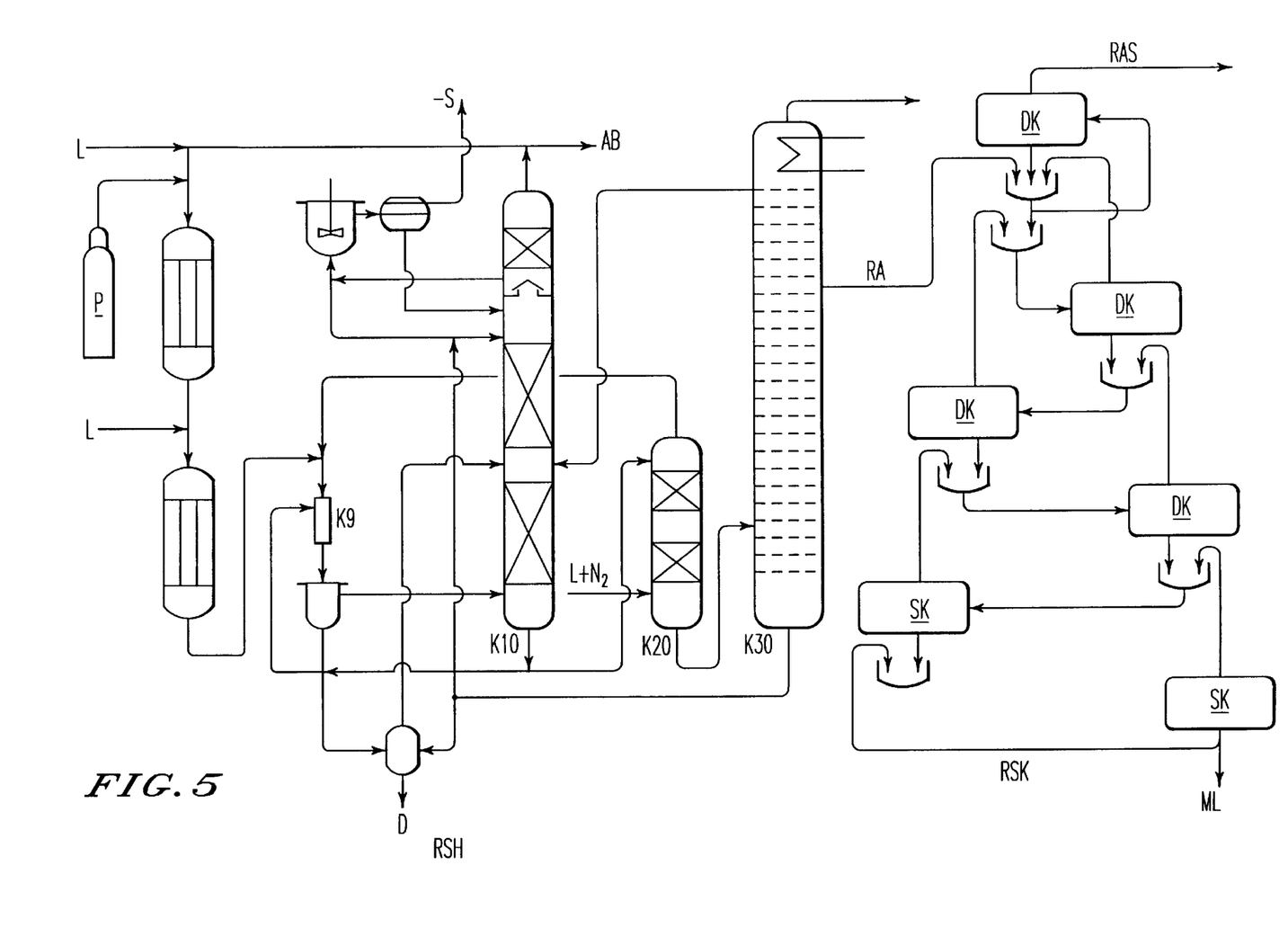
FIG. 5 shows an experimental arrangement as used in Example 1.

The process flow diagram of this example is shown in FIG. 5, with the reference numbers corresponding to those of FIGS. 2 to 4 (additional: dynamic crystallization: DK; static crystallization: SK; mother liquor: ML; pure acrylic acid: RAS; crude acid preparation: RSH; pure acid crystallization: RSK).

426 g/h of crude acrylic acid having a purity of 99.7% by weight were taken off from the side offtake of the distillation column C30.

Two further streams were taken off from the crude acid work-up: 109 g/h of acid water containing 3.2% by weight of acrylic acid and 1 g/h of distillation residue containing 2.5% by weight of acrylic acid. These two streams serve to remove the cocomponents from the system and are therefore discarded. Since these two streams contain acrylic acid, the yield of the crude acid work-up is not 100%, but only 99.2%.

The crude acrylic acid from the column C30 was subsequently purified in one of the above-described crystallization stages. This gave a pure acrylic acid having a purity of 99.95% by weight. The crystallization residue of these purification stages was worked up in 3 dynamic and 2 static crystallization stages. The crystallization residue was concentrated to 4 g/h in these 5 stripping stages and taken from the unit as mother liquor having an acrylic acid content of 76.9% by weight and discarded.

Owing to the loss of acrylic acid via the discarded mother liquor, the yield of the crystallization is only 99.2%.

The total yield is thus 98.4%.

EXAMPLE 2

Figure 6:
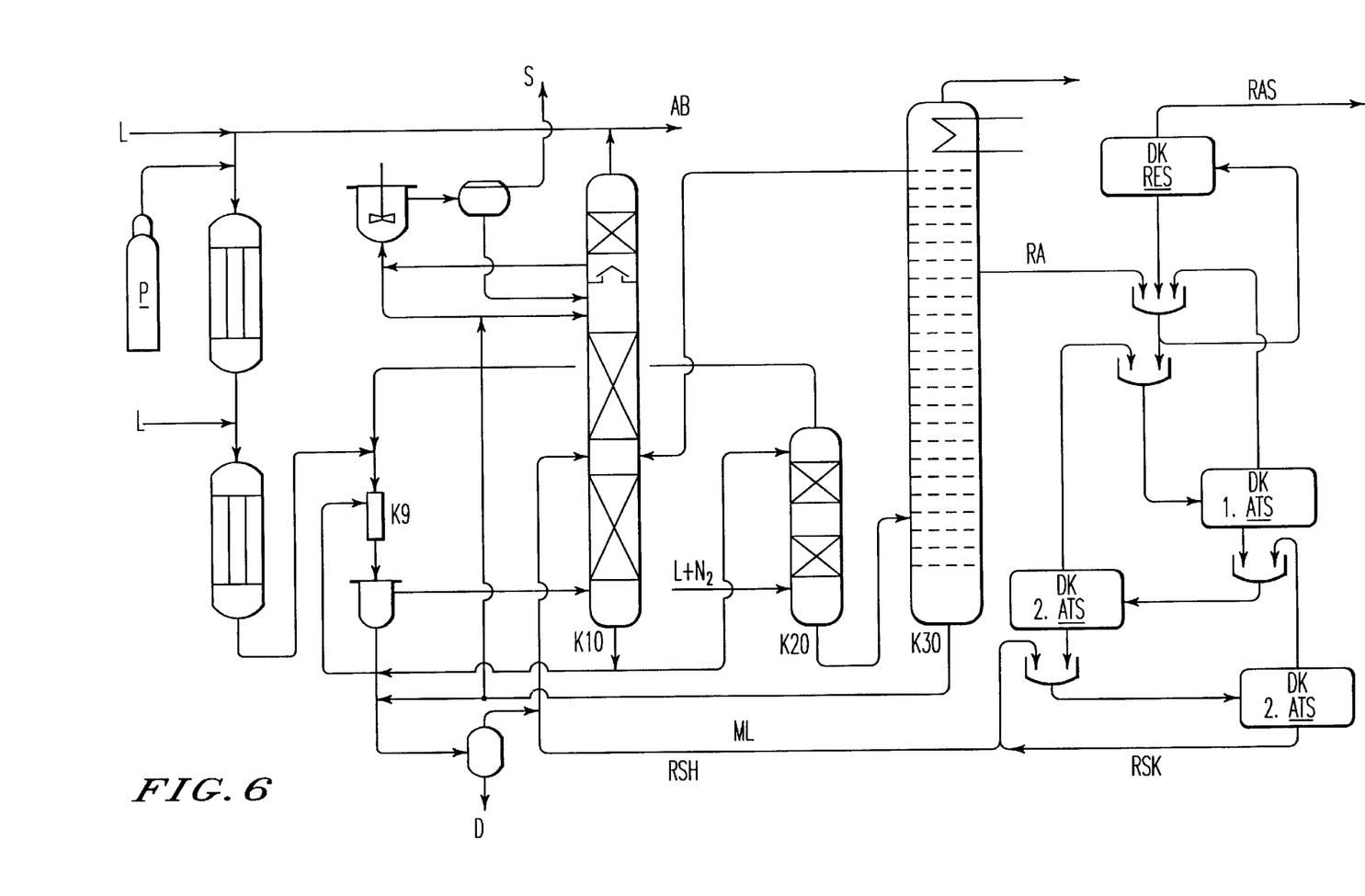
FIG. 6 shows an experimental arrangement as used in Example 2.

This example was carried out using a method similar to Example 1, except that the crystallization residue was worked up only in 3 dynamic crystallization stages and the mother liquor from the crystallization was not discarded but was all recirculated to the column C10 (absorption). The course of the process is shown in FIG. 6, with the reference numbers corresponding to those of FIGS. 2 to 5 (additional: purification stage: RES; stripping stage: ATS).

In this example, 579 g/h (not 426 g/h) of crude acrylic acid having a purity of 99.7% by weight were obtained from the side offtake of the column C30.

The crude acid work-up gave, as in Example 1, 109 g/h of acid water, which in this case contained 2.9% by weight of acrylic acid, and 1 g/h of distillation residue. The yield of the crude acid work-up was 99.3%.

The crude acrylic acid from the column C30 was purified as in Example 1. This gave a pure acrylic acid having a purity of 99.90% by weight. The crystallization residue of this purification stage was concentrated to 156 g/h in the 3 dynamic stripping stages. All of this mother liquor having an acrylic acid content of 98.9% by weight was recirculated to the is column C10.

Owing to the recirculation of the mother liquor, no loss occurs in the crystallization. The total yield is thus 99.5%.

EXAMPLE 3

Example 3 was carried out using a method similar to Example 1, except that 50% of the mother liquor from the crystallization was recirculated to the column C10.

428 g/h instead of 426 g/h of crude acrylic acid having a purity of 99.7% by weight were obtained from the side offtake of the distillation column C30.

109 g/h of acid water containing 2.9% by weight of acrylic acid and 1 g/h of distillation residue containing 2.8% by weight of acrylic acid were taken off from the crude acid work-up. The yield of the crude acid work-up was thus 99.3%.

The crude acrylic acid from the distillation column C30 had, after purification (as in Example 1), a purity of 99.95% by weight. The crystallization residue was concentrated to 4 g/h of mother liquor having an acrylic acid content of 76.1% by weight in the three dynamic and two static stripping stages. Half of this was recirculated to the column C10 and the other half was discarded.

The total yield was thus 90.0%.

The results of Examples 1 to 3 are summarized in the table below. In all examples, the content of propionic acid and acetic acid in the pure acrylic acid was below 500 ppm.

TABLE

Example 1 (comparison): Without recirculation of the mother liquor
Amount Acrylic acid Crude acid work-up

| | | |
|---|---|---|
| Crude acrylic acid | 426 g/h | 99.7% by weight |
| Loss of acid water | 109 g/h | 3.2% by weight |
| Loss of distillation residue | 1 g/h | 2.5% by weight |
| Yield for crude acid work-up | 99.2% | |

Crystallization

| | | |
|---|---|---|
| Pure acrylic acid | 422 g/h | 99.95% by weight |
| Loss of mother liquor | 4 g/h | 76.9% by weight |
| Yield for crystallization | 99.2% | |
| Total yield | 98.4% | |

Example 2: Recirculation of all the mother liquor
Amount Acrylic acid

Crude acid work-up

| | | |
|---|---|---|
| Crude acrylic acid | 579 g/h | 99.7% by weight |
| Loss of acid water | 109 g/h | 2.9% by weight |
| Loss of distillation residue | 1 g/h | 2.8% by weight |
| Yield for crude acid work-up | 99.3% | |

Crystallisation

| | | |
|---|---|---|
| Pure acrylic acid | 425 g/h | 98.9% by weight |
| Recirculated mother liquor | 156 g/h | |
| Yield for crystallization | 73.5% | |
| Total yield | 99.5% | |

Example 3: Partial recirculation of the mother liquor
Amount Acrylic acid

Crude acid work-up

| | | |
|---|---|---|
| Crude acrylic acid | 428 g/h | 99.7% by weight |
| Loss of acid water | 109 g/h | 2.9% by weight |
| Loss of distillation residue | 1 g/h | 2.8% by weight |
| Field for crude acid work-up | 99.3% | |

Crystallization

| | | |
|---|---|---|
| Pure acrylic acid | 423 g/h | 99.95% by weight |
| Mother liquor from static crystallization | 4 g/h | 76.1% by weight |
| Recirculated mother liquor | 2 g/h | 76.1% by weight |
| Yield for crystallization | 99.2% | |
| Total yield | 99.0% | |

We claim:

1. A process for preparing acrylic acid or methacrylic acid, which process comprises the following stages:
   (I) catalytic gas-phase oxidation of propene or isobutene and/or acrolein or methacrolein to acrylic acid or methacrylic acid, to form a gaseous reaction product containing the acid,
   (II) absorption of said reaction product using a high-boiling solvent,
   (III) separation of the loaded solvent from stage (II) into the solvent and a crude acid by means of distillation,
   (IV) purification of the acrylic acid or methacrylic acid from the crude acid from distillation stage (III) by means of dynamic crystallization, static crystallization or a combination of dynamic and static crystallization, with the resulting mother liquor being recirculated at least partly to the absorption stage (II) or the distillation stage (III).

2. A process as claimed in claim 1, wherein the mother liquor of stage (IV) is recirculated to the absorption stage (II).

3. A process as claimed in claim 1, wherein the reaction product comprises acrylic acid and, as impurities, essentially at least one of the compounds selected from the group consisting of aldehydes, propionic acid and acetic acid.

4. A process as claimed in claim 1, wherein the crystallization in stage (IV) is a dynamic crystallization.

5. A process as claimed in claim 1, wherein the crystallization in stage (IV) is a combined dynamic and static crystallization, with the residue of the dynamic crystallization being fed to the static crystallization and the crystallized material from the static crystallization being fed to the dynamic crystallization.

6. A process as claimed in claim 4, wherein the dynamic crystallization is carried out by means of an apparatus which is completely filled by the material flowing through or a falling film crystallizer.

7. A process as claimed in claim 4, wherein the dynamic crystallization is carried out as a countercurrent crystallization.

8. A process as claimed in claim 5, wherein the dynamic and static crystallization are carried out as a countercurrent crystallization.

9. A process as claimed in claim 1, wherein, in stage (II), the high-boiling solvent used is a mixture of diphenyl ether and biphenyl.

10. A process as claimed in claim 1, wherein, in stage (III), crude acid is taken off by means of a side offtake from the column used for the distillation.

11. A process as claimed in claim 3, wherein said reaction product contains from 98 to 99.8% by weight of acrylic acid and from 0.2 to 2% by weight impurities.

12. A process as claimed in claim 3, wherein said reaction product comprises from 98.5 to 99.5% by weight acrylic acid and from 0.5 to 1.5% by weight impurities.

* * * * *